United States Patent
Ogle et al.

(10) Patent No.: US 7,410,797 B2
(45) Date of Patent: Aug. 12, 2008

(54) MENINGEAL-DERIVED STEM CELLS

(76) Inventors: Roy C. Ogle, 415 Hickory Dr., Earlysville, VA (US) 22936; Sunil Tholpady, 32 East Range, Charlottesville, VA (US) 22903

( * ) Notice: Subject to any disclaimer, the term of this patent is extended or adjusted under 35 U.S.C. 154(b) by 366 days.

(21) Appl. No.: 10/458,102

(22) Filed: Jun. 10, 2003

(65) Prior Publication Data

US 2004/0014211 A1    Jan. 22, 2004

Related U.S. Application Data

(60) Provisional application No. 60/387,793, filed on Jun. 11, 2002.

(51) Int. Cl.
*C12N 5/00* (2006.01)
*C12N 5/08* (2006.01)

(52) U.S. Cl. .................. 435/325; 435/368; 435/377

(58) Field of Classification Search .............. 435/325, 435/347, 352, 363, 368
See application file for complete search history.

(56) References Cited

U.S. PATENT DOCUMENTS

| | | | |
|---|---|---|---|
| 5,356,807 A | | 10/1994 | Blass et al. |
| 5,605,938 A | * | 2/1997 | Roufa et al. ............ 514/59 |
| 5,658,786 A | * | 8/1997 | Smith et al. ............ 435/365 |
| 5,849,585 A | | 12/1998 | Mather et al. |
| 5,912,259 A | * | 6/1999 | Carroll et al. ............ 514/369 |

OTHER PUBLICATIONS

Lam RMY et al. 1981. Osteosarcoma of meninges: clinical, light, and ultrastructural observations of a case. Am J Surg Path 5: 203-208.*
Oruckaptan HH et al. 2001. Parafalcine chondrosarcoma: an unusual localization for a classical variant. Surg Neurol 55: 174-179.*
Sugita Y et al. 2000. Primary meningeal sarcomas with leiomyoblastic differentiation. Am J Surg Path 24: 1273-1278.*
Salibi SS et al. 1989. Lipomeningioma: report of three cases and review of the literature. Neurosurgery 25: 122-126.*
Tamamaki N. 2002. Radial glias and radial fibers: what is the function of radial fibers? Anat Sci International 77: 2-11.*
Horwitz EM. 2003. Stem cell plasticity: the growing potential of cellular therapy. Arch Med Res 34: 600-606.*
L.A. Opperman et al., "Tissue interactions with underlying dura mater inhibit osseous obliteration of developing cranial sutures," *Dev. Dynamics*, 198(4):312-322 (1993).
D.B. Drake et al., "Calvarial deformity regeneration following subtotal craniectomy for craniosynostosis: a case report and theoretical implications," *J. Craniofacial Surg.*, 4(2):85-90 (1993).
C.S. Potten et al., "Stem cells: attributes, cycles, spirals, pitfalls and uncertainties. Lessons for and from the crypt," *Development—Supp.*, 110(4):1001-20 (1990).
G.M. Morriss-Kay, "Derivation of the mammalian skull vault," *J. Anat.*, 199:143-151 (2001).
S.S. Tholpady et al., "Mesenchymal Stem Cells From Rat Visceral Fat Exhibit Multipotential Differentiation In Vitro," *Anat. Rec.*, 272A:398-402 (2003).
Greenwald, Joshua A. et al., "Regional Differentiation of Ctanial Suture-Associated Dura Mater In Vivo and In Vitro: Implications for Suture Fusion and Patency," *Journal of Bone and Mineral Research*, vol. 15, No. 12, pp. 2413-2430, (2000).
Woodbury, Dale, et al., "Adult Rat and Human Bone Marrow Stromal Cells Differentiate Into Neurons," *Journal of Neuroscience Research*, 61:364-370 (2000).
Sanchez-Ramos et al., "Differentiation of Neuron-like Cells from Bone Marrow Stromal Cells," *Movement Disorders*, vol. 13, supplement 2, p. 122 (1998). Abstract Only.
Pittenger et al., "Multilineage Potential of Adult Human Mesenchymal Stem Cells," *Science*, vol. 284, pp. 143-147 (1999).
S. S. Tholpady, et al., Mesenchymal Stem Cells From Rat Visceral Fat Exhibit Multipotential Differentiation In Vitro, The Anatomical Record Part A, Wiley-Liss, Inc., pp. 398-402, (2003).
Mark F. Pittenger, et al., Multilineage Potential of Adult Human Mesenchymal Stem Cells, SCIENCE, pp. 143-147, (Apr. 2, 1999).
Patricia A. Zuk, Ph.D., et al., Multilineage Cells from Human Adipose Tissue: Implications for Cell-Based Therapies, Tissue Engineering, vol. 7 (No. 2), pp. 211-228, (2001).

* cited by examiner

*Primary Examiner*—Sandra E. Saucer
*Assistant Examiner*—Lora E Barnhart
(74) *Attorney, Agent, or Firm*—Seth D. Levy; Davis Wright Tremaine LLP

(57) ABSTRACT

Stem cell lines derived from meningeal tissue such as dura mater, pia mater, or arachnoid mater, are disclosed. In various embodiments, the stem cell lines include greater than 80%, greater than 90%, or greater than 99% of pluripotent meningeal-derived stem cells. In other embodiments, the stem cell lines are induced to form nerve cells, bone cells, cartilage cells, Schwann cells, adipocytes, fibroblasts, or melanocytes with various inducing agents, such as antioxidants, steroid hormones, laminin, or various growth factors. Derivation of the current stem cell lines is accomplished through explantation or enzymatic dissociation of meningeal tissue, followed by expansion to large populations using growth media.

21 Claims, 4 Drawing Sheets
(3 of 4 Drawing Sheet(s) Filed in Color)

MENINGEAL-DERIVED STEM CELLS

RELATED APPLICATIONS

This application claims the benefit of priority under 35 U.S.C. § 119 of provisional U.S. application Ser. No. 60/387,793, filed Jun. 11, 2002, the contents of which are hereby incorporated by reference.

GOVERNMENT RIGHTS

This invention was made with United States Government support under Grant No. SR01 DE010369 awarded by the National Institutes of Health. The United States Government has certain rights in the invention.

FIELD OF THE INVENTION

The present invention is directed to stem cells and methods of preparing populations of progenitor cells that differentiate into a preselected cell type with high efficiency.

BACKGROUND OF THE INVENTION

The brain and spinal cord are enclosed and protected by the meninges; tough and fibrous tissues comprising the dura mater and pia mater. Developmentally, these tissues form partly from the neural crest; a class of highly migratory and plastic cells that also form several diverse tissue types, such as bone, cartilage, muscle, gut, adrenal glands, etc. The dura mater has been shown to regulate bone formation in the developing skull through tissue interactions mediated by growth factors originating in the dura (L. A. Opperman et al., "Tissue interactions with underlying dura mater inhibit osseous obliteration of developing cranial sutures," *Dev. Dynamics*, 198(4):312-322 (1993)). During skull regeneration in humans and animals whose heads are still growing, the bone and other connective tissues of the skull are formed from cellular precursors in the dura (FIG. 1; D. B. Drake et al., "Calvarial deformity regeneration following subtotal craniectomy for craniosynostosis: a case report and theoretical implications," *J. Craniofacial Surg.*, 4(2):85-90 (1993)).

Moreover, there is extensive interest in developing methods for using pluripotential stem cell populations for a wide variety of potential therapeutic applications, including delivery of therapeutic genes, correction of gene defects, replacement/augmentation of existing dysfunctional cell populations (e.g., dopaminergic neurons in Parkinsons Disease), and generation of organs/tissues for surgical repair/replacement. However, existing methods in the field have a number of major limitations that relate to obtaining purified populations of the desired cell types from pluripotent stem cells. By way of example, embryonic stem cells pose interesting possibilities as several studies show that these cells are pluripotent, however, the use of these cells is mired in ethical and political considerations. It is therefore likely that this technology will not be available for use in the near future.

There is a need in the art for a stem cell population that obviates the limitations of currently available stem cells; thereby enabling further research in this field, and also the therapeutic, clinical use of stem cells in various aspects of biomedicine. The present invention is directed to such a novel stem cell population, which is isolated from meningeal tissues. This stem cell population has properties that provide significant advantages over the stem cells currently available.

SUMMARY OF THE INVENTION

One aspect of the present invention is directed to stem cells derived from the dura mater, the pia mater or the arachnoid mater, as well as methodologies for isolation, differentiation and explantation of these cells. Meningeal tissue may be explanted (i.e., cells migrate out of adherent pieces of tissue) or enzymatically dissociated to yield primitive mesenchymal cells. The tissues may include those removed by biopsy from a patient or tissues removed aseptically from a fetus. These cells exhibit characteristics of "adult" stem cells or progenitors: robust self-renewal and a high degree of developmental plasticity. The stem cells may be readily propagated in culture (showing little senescence after 20 passages), and are capable of differentiating into various cell types. Thus, the meningeal-derived stem cells of the present invention are multipotent.

The meningeal stem cells of the present invention can be taken from a small biopsy, and rapidly expanded to large populations of cells using a specially defined media that maintains their undifferentiated state. Transformation to neural cells can be accomplished rapidly (i.e., within several hours) and bone and cartilage within two weeks, by adding factors that support and maintain these cell phenotypes. Schwann cells, adipocytes and fibroblasts may be rapidly produced, as well. In addition, the number of cells that transform to a neural morphology is between 90% and 95%. Thus, these cells may have particular utility in treating central nervous system (CNS) degenerative disorders and spinal cord injuries. The rapid proliferative capacity and high rate of neuronal differentiation makes these applications well-suited for the stem cells, although numerous other applications exist, as well.

In another aspect of the present invention, the use of stem cells derived from the dura mater, the pia mater or the arachnoid mater in biomedical applications is described. For example, the stem cells of the present invention may be used for tissue regeneration, gene and drug delivery and cell replacement therapies. They may find additional applications in research settings, as well as alternate therapeutic modalities or clinical treatments.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1A depicts the dura mater of a newborn rat; FIG. 1B depicts the dura cells of a newborn rat; FIG. 1C depicts the dura cells (exposed to dexamethasone) of a newborn rat; and FIG. 1D depicts the dura mater, pia mater and meninges of a newborn rat. FIG. 1E depicts the frontal and parietal bones of a human infant skull, and FIG. 1F depicts the dura mater and osteogenic front of a human fetal skull.

FIG. 2A depicts meningeal cells on a tissue culture plate; their flattened morphology is apparent. FIG. 2B depicts meningeal cells exposed to steroid treatment; extensive branching and dendritic morphologies are apparent. FIG. 2C depicts meningeal cells exposed to antioxidant treatment; cells are mostly bipolar-type neuronal morphologies.

FIGS. 3A and 3B depict untreated meningeal cells showing no staining for alkaline phosphatase at low and high magnification, respectively. FIGS. 3C and 3D depict meningeal cells plated onto MATRIGEL, showing intense staining for alkaline phosphatase in cell condensations following two weeks in culture.

DETAILED DESCRIPTION OF THE INVENTION

Figure 1:
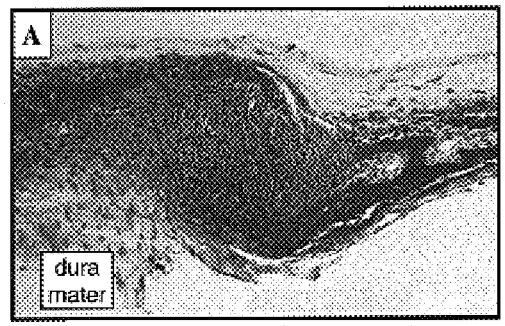
FIG. 1 is executed in color, and illustrates a histological identification of the meninges and cells within a newborn rat, in human tissue and in human fetal tissue, in accordance with an embodiment of the present invention.
Figure 1:
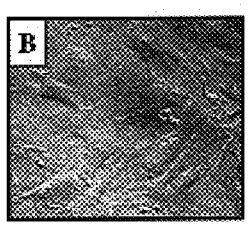
Figure 1:
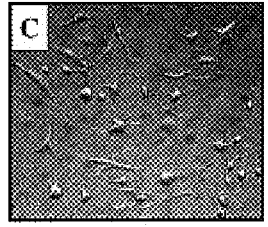
Figure 1:
Figure 1:
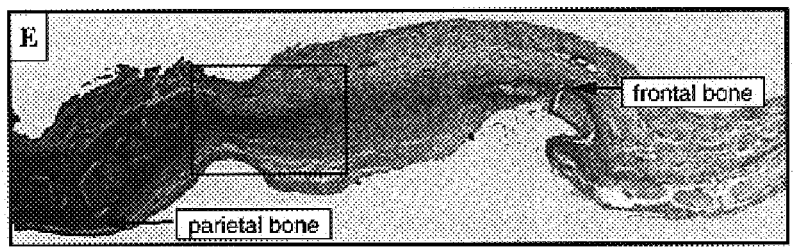
Figure 1:
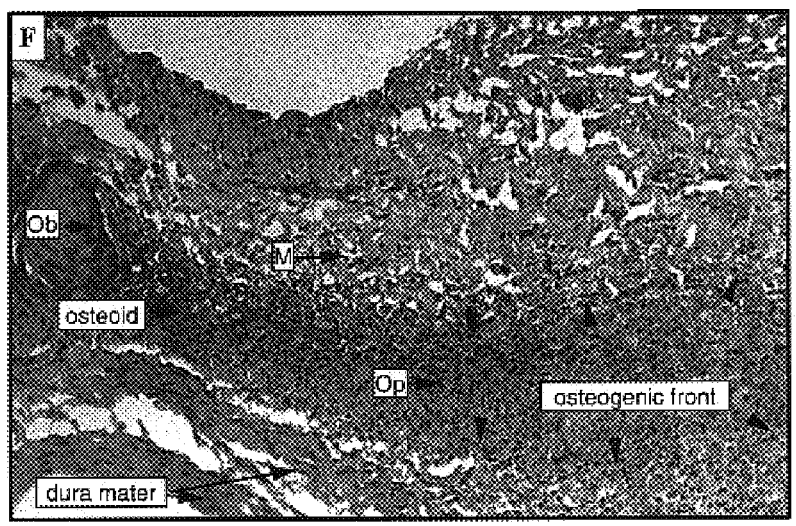

In describing and claiming the invention, the following terminology will be used in accordance with the definitions set forth below.

As used herein, "nucleic acid," "DNA," and similar terms also include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention.

As used herein a "gene" refers to the nucleic acid coding sequence as well as the regulatory elements necessary for the DNA sequence to be transcribed into messenger RNA (mRNA) and then translated into a sequence of amino acids characteristic of a specific polypeptide.

A "marker" is an atom or molecule that permits the specific detection of a molecule comprising that marker in the presence of similar molecules without such a marker. Markers include, for example radioactive isotopes, antigenic determinants, nucleic acids available for hybridization, chromophors, fluorophors, chemiluminescent molecules, electrochemically detectable molecules, molecules that provide for altered fluorescence-polarization or altered light-scattering and molecules that allow for enhanced survival of an cell or organism (i.e. a selectable marker). A reporter gene is a gene that encodes for a marker.

As used herein, the term "purified" and like terms relate to the isolation of a molecule or compound in a form that is substantially free of contaminants normally associated with the molecule or compound in a native or natural environment.

As used herein the term "pharmaceutically acceptable carrier" encompasses any of the standard pharmaceutical carriers, such as phosphate buffered saline (PBS), water and emulsions such as an oil/water or water/oil emulsion, and various types of wetting agents.

As used herein the term "totipotent" or "totipotential" and like terms refers to cells that have the capability of developing into a complete organism or differentiating into any cell type of that organism.

As used herein the term "pluripotent" or "pluripotential" and like terms refers to cells that cannot develop into a complete organism, but retain developmental plasticity, and are capable of differentiating into some of the cell types of that organism.

As used herein a "differentiated cell type" refers to a cell that expresses gene products that are unique to that cell type. For example, a nerve cell is a cell type that expresses specific markers associated with smooth muscle cells, including β-III tubulin and neuron specific enolase (NSE).

The present invention is based on the inventors' surprising discovery that stem cell populations may be derived from the meninges. More specifically, the present invention is directed to compositions comprising purified meningeal stem cells, and, more particularly, stem cells isolated from the dura mater, pia mater or arachnoid mater, as well as methodologies for the isolation, differentiation and explantation of such stem cells. These stem cells may be used in accordance with the present invention in a wide variety of biomedical applications, including, but in no way limited to, tissue regeneration, gene and drug delivery and cell replacement therapies. The cells are unusual not only in their anatomical location (the meninges have not heretofore been identified as a source of stem cells), but also in their behavior—the stem cells of the present invention are believed to be the only stem cells that differentiate into osteoblasts without dexamethasone treatment. In fact, the stem cells of the present invention differentiate into neuronal cells in media containing dexamethasone, while all other stem cells differentiate into osteoblasts under similar treatment conditions.

The invention includes the generation of multiple cell types from the multipotent cell or cells that reside in the meningeal tissues surrounding and associated with the brain and spinal cord. In particular, the invention is directed to the derivation of stem cells from these tissues and the differentiation of these stem cells into cell types beyond those that are normally associated with the meninges. Although the procedures described herein produce a total population of cells, individual, clonal cell lines may be derived from the total population. Large quantities of cells may be grown and harvested with the methods of the present invention for applications in, for example, gene, drug and molecule screening and delivery, tissue engineering, regeneration and replacement of nerve, bone, cartilage, muscle, fat and other organs, and treatment of spinal cord injury and CNS disorders such as Parkinson's disease, Alzheimer's disease, dementia and multiple sclerosis. Replacement or regeneration of tissue damaged through a variety of physiologic and pathologic processes including aging, cancer, trauma, infection, and congenital anomalies is an area of active and intense investigation, and may also be within the scope of conditions that may be addressed with the stem cells of the present invention. In accordance with yet another embodiment of the present invention, in vitro treatment includes insertion of a gene construct for delivery on implantation of the cells of the present invention.

In accordance with one embodiment of the present invention, a composition comprising a substantially pure population of totipotent or pluripotent cells is provided. The composition may include a pharmaceutically acceptable carrier. In preferred embodiments, the substantially pure population of cells comprises greater than 80% of totipotent or pluripotent cells; more preferably greater than 90% of totipotent or pluripotent cells; and most preferably a purity of 99% or 100% of totipotent or pluripotent cells. In one embodiment, a purified population of meningeal-derived stem cells is provided, wherein greater than 60% of the cells are induced to form nerve cells, bone cells, cartilage cells, Schwann cells, adipocytes and fibroblasts by contacting the cells with a nerve cell, bone cell, cartilage cell, Schwann cell, adipocyte or fibroblast inducing agent, respectively.

The tissues for isolation of the stem cells may include those removed by biopsy from patients or tissues removed aseptically from fetuses by any of a host of methodologies that will be readily understood and may be routinely performed by those of skill in the art. By way of example, meningeal stem cells may be prepared by obtaining a small, full thickness piece of tissue from the meninges surrounding the brain or spinal cord. This piece of tissue may include, e.g., an approximately 4 mm punch biopsy. Alternatively, dural cells that adhere to calvarial fragments (e.g., those removed as autologous grafting materials or for burr holes during neurosurgery) may be suitable for use as a piece of tissue in connection with the methods of the present invention.

In a further embodiment of the present invention, a method is provided for isolating meningeal stem cells by enzymatic digestion. The tissue may first be washed in a physiologic buffer (e.g., PBS or Hanks balanced salt solution), and then placed in the same solution containing collagenase (300U) for a predetermined length of time to dissociate the tissue (typically the tissue is treated for about 5 to 30 minutes, and more preferably for about 15 minutes, at approximately 37° C.). The resultant dissociated tissue is then recovered, typically by centrifuging the tissue and washing the resultant pellet. The pellet is then plated onto tissue culture dishes containing a growth medium. Preferably, the growth medium includes Dulbecco's Modified Eagle Medium (DMEM), approximately 10% fetal bovine serum (FBS) and approximately 1% glutamine. The tissue culture substrate can include, but is not limited to, tissue culture plate plastic, polyamino acids, fibronectin, type I collagen and various forms of laminin (e.g., pure mouse laminin-1 or MATRIGEL); all forms of laminin being hereinafter included: in the term "laminin." By way of example, MATRIGEL (available from BD Biosciences Discovery Labware; Bedford, Mass.; hereinafter "BD Biosciences") is over 90% laminin-1, with the remaining portion including a mixture of type IV collagen, perlecan and nidogen/entactin. This preparation is extracted from the Engelbreth-Holm-Swarm (EHS) tumor of mice and is subjected to multiple 45% ammonium sulfate precipitation to remove growth factors. The use of laminin substrates is well known in the art, and, by way of example, is described in L. A. Davis et al, "Embryonic heart mesenchymal cell migration on laminin," *Dev. Biol.*, 133:37-43 (1989); T. M. Sweeney et al., "Laminin potentiates differentiation of PCC4azal embryonal carcinoma into neurons," *J. Cell Sci.*, 97:3-31 (1990); and T. M. Sweeney et al., "Repair of critical size rat calvarial defects using extracellular matrix gels," *J. Neurosurg.*, 83(4):710-715 (1995).

In an alternate explantation isolation technique, the tissue may be placed on the culture substrate with a minimal amount of medium where it is allowed to adhere firmly; stem cells grow out of the tissue onto the plate. As used herein, a "minimal amount" of medium is a volume of medium sufficient to cover the tissue, preventing drying, but not so much that the tissue will float or become dislodged from the substrate before cells begin to emigrate. Conversely, an "excessive amount" of medium is a volume of medium in which the tissue floats and cells are unable to contact the substrate; disadvantageous for explant outgrowth. Plastic or laminin-covered culture substrates may be particularly advantageous in this alternate isolation technique.

The stem cells that attach and grow in the culture dishes or plates may be subcultured and expanded for several generations. Cells may be passaged when they become 70-80% confluent, and are not allowed to become completely confluent (although this does not appear to alter differentiation capacity in the short term). No changes were observed in the cells' doubling behavior or cell characteristics over the longest culture period studied (i.e., sixty population doublings).

The self-renewal capacity that these cells demonstrate is one of the characteristics common to all stem cells. Because the cells possess a self-renewal capacity, it is not necessary (although still possible and may be particularly useful if these cells are studied as cell lines) to immortalize the cells using one of the many transfection techniques commonly used in the art. These techniques may be used to transfer genes of interest into the meningeal stem cells. Self-maintenance is but one of several characteristics that stem cells possess. Additionally, they have the capacity to proliferate, to produce of a large number of differentiated functional progeny, and to regenerate target tissue after injury. Moreover, stem cells are generally flexible with respect to the aforementioned functional capabilities (C. S. Potten et al., "Stem cells: attributes, cycles, spirals, pitfalls and uncertainties. Lessons for and from the crypt," *Development—Supp.*, 110(4):1001-20 (1990)).

While not wishing to be bound by any theory, it is believed that the developmental origin of the meningeal cells as neural crest derivatives confers multipotent differentiation capacity to the cells. In accordance with various embodiments of the present invention, the inventors have exploited this capacity of cells derived from the dura mater to produce nerve, bone, cartilage and Schwann cells, as well as adipocytes and fibroblasts. In alternate embodiments of the present invention, meningeal-derived cells may be turned into melanocytes and a variety of neural supporting cells and muscle cell types.

There are several advantages to using meningeal-derived stem cells in clinical biomedicine and research applications, as opposed to other stem cell variants. The cells of the present invention are a reservoir of developmental potential unique from any previously described and will increase the armamentarium available for stem cell-based therapies. A major advantage of this particular stem cell is its capacity to differentiate into neural cells at a higher rate and greater percentage than either bone marrow stem cells or fat-derived stem cells (the other major adult stem cells known to form neurons). As such, purer stem cell populations can be implanted sooner into a damaged CNS than could be achieved with other adult-derived stem cells. Additionally, purer populations are believed to be advantageous because there is a larger biomass that actively participates in restoration and regeneration.

Another advantage of the cells of the present invention is that they can be derived from adult as well as fetal tissues. Thus, there are fewer ethical or legal implications in their use than with stem cells from embryonic and early fetal sources. Another advantage relative to embryonic stem cells is that the cells of the present invention can be derived from an individual, propagated and differentiated in vitro, and delivered back to the same individual; thereby avoiding rejection issues. These issues limit the use of embryonic stem cells at present. The ability to transplant cells without immunosuppressive drugs is also a major advantage, because these drugs tend to impair wound healing and regenerative capacity. Yet a further advantage of the cells of the present invention is the decreased senescence observed in the cell line, which allows for tremendous expansion—large masses of cells may be produced for transplantation based on only a small biopsy.

EXAMPLES

The following Examples illustrate the differentiation of meningeal-derived stem cells into distinct cell types in vitro.

Cells derived from both the covering of the brain and spinal cord were isolated, cultured and exposed to conditions that caused differentiation into cells with the morphology and specific gene expression of neuroblasts, Schwann cells, osteoblasts, chondrocytes, adipocytes and fibroblasts. The stem cells divide rapidly, with population doubling times of 36 hours; nearly as fast as the fastest primary human cell lines.

Example 1

Preparation of Nerve Cells

Figure 2:
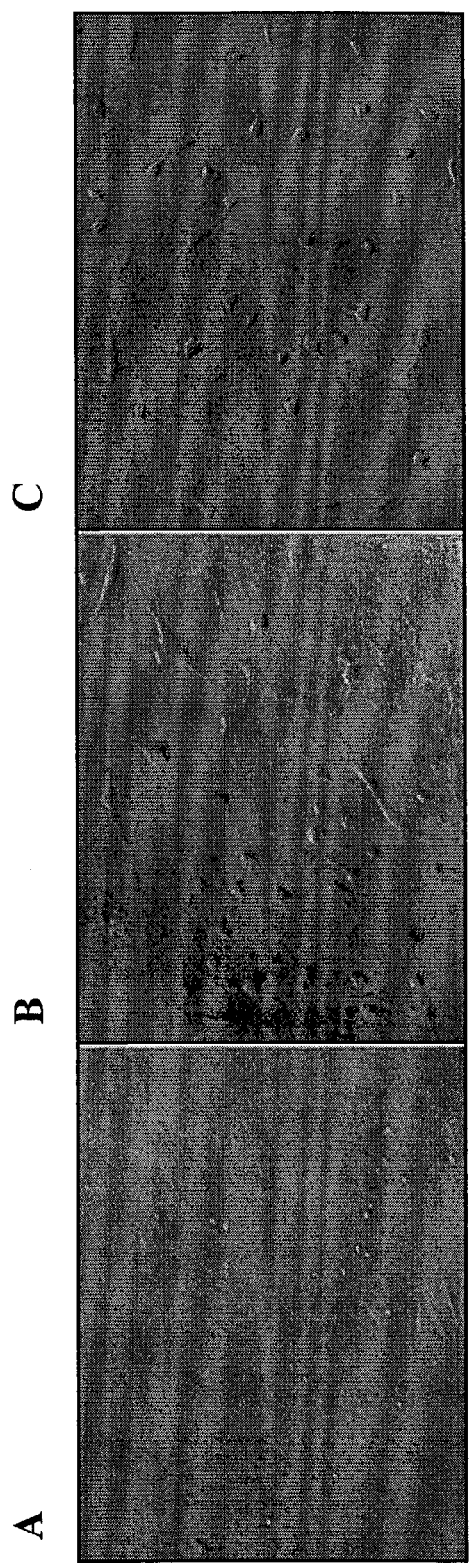
FIG. 2 illustrates the neural differentiation of meningeal-derived stem cells in accordance with an embodiment of the present invention.

Cells from the meninges that are allowed to become 70% confluent (FIG. 2A) are susceptible to differentiating into nerve under two conditions: antioxidant treatment and steroid hormone treatment. When cells are exposed to a neuronal pre-induction media containing an antioxidant (DMEM, 20% FBS, 1 mM β-mercaptoethanol) for 24 hours, followed by treatment with neuronal induction media also containing an antioxidant (DMEM, 5 mM β-mercaptoethanol), the cells differentiate into neural-like cells within six hours (FIG. 2C). This can also be achieved with other antioxidants (i.e., reducing agents), such as butylated hydroxyanisole (BHA) (approximately 200 μM), dithiothreitol (DTT; i.e., Cleland's reagent), as well as dithioerythritol, tributylphosphine, iodoacetamide, tris-phosphine HCl, deoxythymidine-triphosphate trilithium salt, diethylthiatricarbocyanine perchlorate, diethylthiatricarbocyanine iodide and DECROLINE D (available from BASF Corporation; Mount Olive, N.J.; generic name zinc formaldehyde sulfoxylate). These conditions are similar to those used to differentiate bone marrow-derived stem cells and adipose-derived stem cells (D. Woodbury et al., "Adult rat and human bone marrow stromal cells differentiate into neurons," *J. Neuroscience Res.*, 61(4):364-70 (2000)). The cells that form have a bipolar morphology and express nerve-specific markers.

The cells differentiate into what are morphologically distinct subsets of neurons when exposed to small concentrations (e.g, 100 nM) of dexamethasone; a steroid hormone. A neuronal induction media incorporating the same (DMEM, 10% FBS, 100 nM dexamethasone) causes neural differentiation as with the antioxidant media described above, but the cells cultured in this steroid hormone media are highly dendritic and have complex processes reminiscent of neural cells from the CNS (FIG. 2B). These cells also express the specific neuronal marker gene β-III tubulin.

While not truly within the steroid class of compounds, vitamin A and its derivatives (e.g., retinol, retinaldehyde and retinoic acid) act through the steroid response elements and elicited similar effects to dexamethasone, as did 1,25-dihydroxy vitamin $D_3$. These may therefore be used as substitutes for dexamethasone. Other steroids that may be used in accordance with this embodiment of the present invention include pregnenolone, aldosterone, testosterone, estradiol and cortisol.

Neural cell differentiation may also be stimulated with agents that stimulate increased intracellular cyclic AMP, including dibuteryl cAMP (dbcAMP) or iso-butrymethylxanthine in the 0.5-10 mM range.

Example 2

Preparation of Bone Cells

Figure 3:
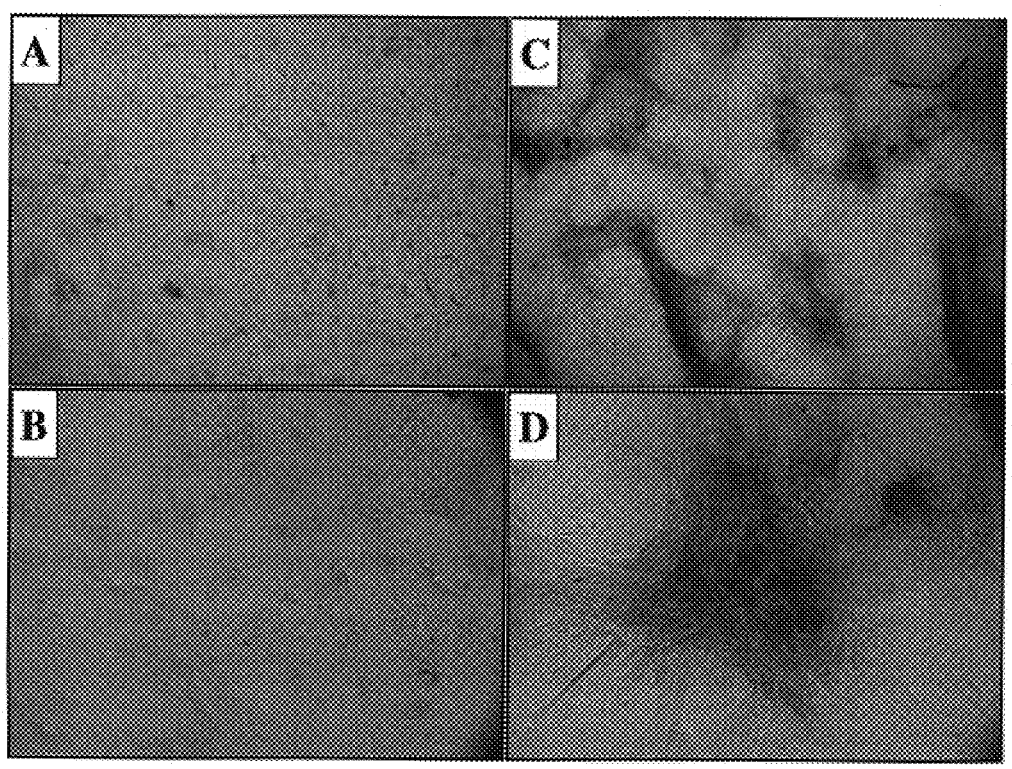
FIG. 3 is executed in color, and illustrates osseous differentiation of meningeal-derived stem cells in accordance with an embodiment of the present invention.

Dural cells were forced to adopt a bony phenotype by two separate methods. The first included plating these cells on a MATRIGEL or laminin substrate (100 μg/cm²). Plated cells expressed alkaline phosphatase (a differentiated bone marker) within seven days, and adopted an osteocytic morphology (FIGS. 3C & 3D). Untreated cells showed no staining for alkaline phosphatase (FIGS. 3A & 3B).

The second method involved exposing the cells to organic and inorganic phosphates. Inorganic phosphates included varying levels (i.e., 3-6 mM) of sodium phosphate and potassium phosphate, and organic phosphates included 10 mM β-glycerol phosphate. In addition, cells were exposed to 50 μg/ml ascorbic acid. Cells under these conditions also expressed alkaline phosphatase (data not shown).

Example 3

Preparation of Cartilage

Figure 4:
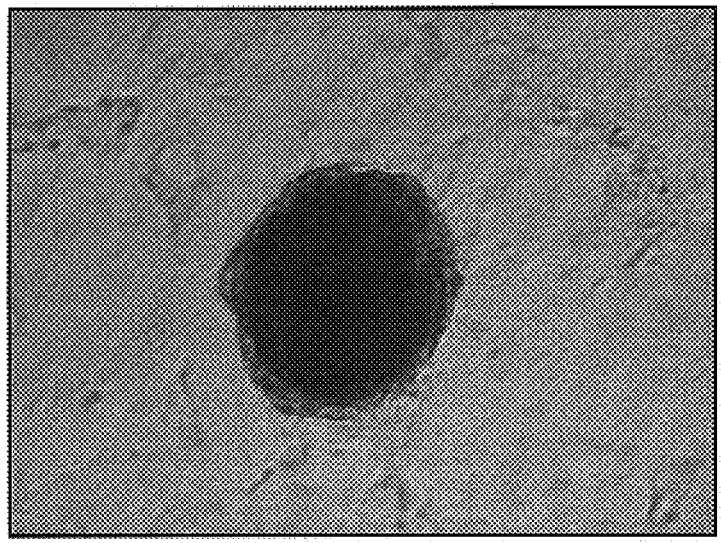
FIG. 4 is executed in color, and illustrates chondrocytic differentiation of meningeal-derived stem cells in accordance with an embodiment of the present invention. Meningeal cells were allowed to grow in micromass culture for four weeks in chondrocytic differentiation media. Nodules were exposed to Alcian Blue, a dye that specifically stains sulfated proteoglycans found in cartilage.

Cartilage development is fundamentally different from other tissues in that complex three-dimensional interactions are required to form nodules of cartilage in vitro. To accomplish this, a 10 μL volume of a $1 \times 10^7$ cells/mL suspension was plated and allowed to attach to a tissue culture surface. This micromass culture differentiated into cartilage within two weeks when placed in media that contained 1X insulin-selenium-transferrin (ITS diluted 100-fold; available under the tradename ITS+ PREMIX from BD Biosciences) and 10 ng/ml transforming growth factor (TGF)-β1. The production of sulfated proteoglycan as demonstrated by Alcian Blue (available from Sigma-Aldrich Co.; St. Louis, Mo.) staining is indicative of chondrocytic differentiation (FIG. 4).

Example 4

Preparation of Schwann Cells

Figure 5:
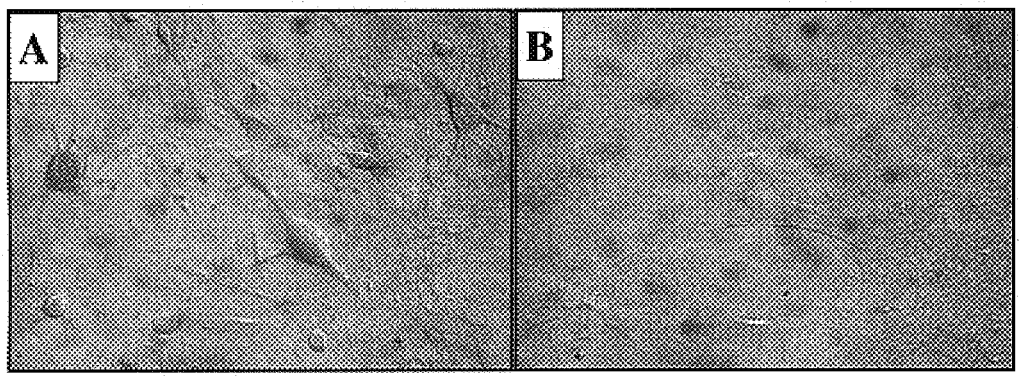
FIG. 5 is executed in color, and illustrates differentiation of meningeal-derived stem cells into Schwann cells in accordance with an embodiment of the present invention. Cells were stained for S-100. Cells treated with a final growth factor treatment step stained more strongly (i.e., were more highly positive) for S-100 (FIG. 5A) as compared with cells that did not receive this final treatment step (FIG. 5B).

The dural stem cells have the capacity to differentiate into nerve support cells or Schwann cells. In response to a multi-day, multi-drug regimen, they became highly positive for S-100, a Schwann cell marker. In addition, they assumed a neuronal phenotype (FIG. 5). The treatments included serum withdrawal, basal medium eagle (BME), retinoids and growth factors. Specifically, a first treatment step included DMEM/1 mM BME, and was administered for one day. A second treatment step included DMEM/10% FBS/70 ng/ml retinoic acid, and was administered for three days. Finally, a third treatment step included DMEM/10% FBS/5 μM forskolin (FSK)/200 ng/ml heregulin (HER)/10 ng/ml basic fibroblast growth factor (bFGF)/5 ng/ml platelet-derived growth factor (PDGF), and was administered for five days. Cells treated with this final treatment step stained more strongly (FIG. 5A) for S-100 than those that were not treated with this treatment step (FIG. 5B).

Schwann cell differentiation may also be stimulated with agents that stimulate increased intracellular cyclic AMP, including dibuteryl cAMP (dbcAMP) or iso-butrymethylxanthine in the 0.5-10 mM range.

Example 5

Preparation of Adipocytes

Adipogenesis was induced in media consisting of basal media (DMEM with 10% FBS), along with the following additives: 1 μM dexamethasone, 10 μM insulin, 200 μM indomethacin and 0.5 mM isobutyl-methylxanthine (IBMX). Multilocular adipocytes positive for peroxisome proliferator-activated receptor (PPAR)-gamma (data not shown) began to appear between one and three weeks following culture preparation.

Example 6

Preparation of Fibroblasts

The undifferentiated cells were grown in basal media (DMEM with 10% FBS) along with 50 mM ascorbic acid. After loading a native type I collagen gel with cells in basal media, a variety of constructs were derived by manipulating: (1) the concentration of collagen (from 1-10 mg/ml); (2) the cross-linking of the collagen by gluteraldehyde treatment; and (3) the type and amount of tensional force applied. By way of example, if the cells were given two fixed points against which they contract, the structure formed resembled a tendon (data not shown). If a sheet of cross-linked collagen sponge was seeded with cells in basal media, the construct resembled the fibroblasts of the dermis (data not shown).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

We claim:

1. A composition, comprising:
   a population of differentiated cells of a cell type selected from the group consisting of a nerve cell, a bone cell, a cartilage cell, a Schwann cell, an adipocyte, a fibroblast, a melanocyte and combinations thereof; and
   a population of adult stem cells isolated from the meninges, wherein said population of differentiated cells is obtained by a process, comprising:
   providing a population of adult stem cells isolated from the meninges; and
   inducing greater than 60% of said population of stem cells isolated from the meninges to differentiate into said population of differentiated cells.

2. The composition of claim 1, wherein said cell type is a nerve cell and wherein inducing greater than 60% of said population of stem cells isolated from the meninges to differentiate comprises culturing said population of stem cells isolated from the meninges with a nerve cell inducing agent selected from the group consisting of antioxidant treatment, steroid hormone, vitamin A, retinal, retinaldehyde, retinoic acid, 1,25-dihydroxy vitamin $D_3$, an agent capable of stimulating intracellular cyclic AMP and combinations thereof.

3. The composition of claim 2, wherein said nerve cell inducing agent is an antioxidant treatment comprising an antioxidant selected from the group consisting of β-mercaptoethanol, butylated hydroxyanisole (BHA), dithiothreitol (DTT), dithioerythritol, tributylphosphine, iodoacetamide, tris-phosphine HCl, deoxythymidine-triphosphate trilithium salt, diethylthiatricarbocyanine perchiorate, diethylthiatricarbocyanine iodide and combinations thereof.

4. The composition of claim 2, wherein said nerve cell inducing agent is a steroid hormone selected from the group consisting of dexamethasone, pregnenolone, aldosterone, testosterone, estrad iol, cortisol and combinations thereof.

5. The composition of claim 4, wherein said steroid hormone is dexamethasone.

6. The composition of claim 2, wherein said nerve cell inducing agent is selected from the group consisting of vitamin A, retinol, retinaldehyde, retinoic acid, 1,25-dihydroxy vitamin $D_3$ and combinations thereof.

7. The composition of claim 1, wherein said cell type is a bone cell, and wherein inducing greater than 60% of said population of stem cells isolated from the meninges to differentiate comprises culturing said population of stem cells isolated from the meninges with a bone cell inducing agent comprising laminin.

8. The composition of claim 1, wherein said cell type is a bone cell, and wherein inducing greater than 60% of said population of stem cells isolated from the meninges to differentiate comprises culturing said population of stem cells isolated from the meninges with a bone cell inducing agent selected from the group consisting of organic phosphates, inorganic phosphates, ascorbic acid and combinations thereof.

9. The composition of claim 1, wherein said cell type is a cartilage cell, and wherein inducing greater than 60% of said population of stem cells isolated from the meninges to differentiate comprises culturing said population of stem cells isolated from the meninges with a cartilage cell inducing agent selected from the group consisting of an insulin-selenium-transferrin composition, transforming growth factor (TGF)-β1 and combinations thereof.

10. The composition of claim 1, wherein said cell type is a Schwann cell, and wherein inducing greater than 60% of said population of stem cells isolated from the meninges to differentiate comprises using a Schwann cell inducing treatment regimen, comprising:
    administering to said population of stem cells isolated from the meninges a first treatment, comprising Dulbecco's modified eagle medium (DMEM) and basal medium eagle (BME); and
    administering to said population of stem cells isolated from the meninges a second treatment, comprising DMEM, fetal bovine serum (FBS) and retinoid acid.

11. The composition of claim 10, wherein said treatment regimen further comprises:
    administering to said population of stem cells isolated from the meninges a third treatment, comprising DMEM, FBS, forskolin (FSK), heregulin (HER), basic fibroblast growth factor (bFGF) and platelet-derived growth factor (PDGF).

12. The composition of claim 11, wherein said first treatment is administered for about one day, said second treatment is administered for about three days and said third treatment is administered for about five days.

13. The composition of claim 1, wherein said cell type is a Schwann cell, and wherein inducing greater than 60% of said population of stem cells isolated from the meninges to differentiate comprises culturing said population of stem cells isolated from the meninges with a Schwann cell inducing agent that stimulates intracellular cyclic AMP.

14. The composition of claim 1, wherein said cell type is an adipocyte, and wherein inducing greater than 60% of said population of stem cells isolated from the meninges to differentiate comprises culturing said population of stem cells isolated from the meninges with an adipocyte inducing agent comprising dexamethasone, insulin, indomethacin and isobutyl-methylxanthine (IBMX).

15. The composition of claim 1, wherein said cell type is a fibroblast, and wherein inducing greater than 60% of said population of stem cells isolated from the meninges to differentiate comprises culturing said population of stem cells isolated from the meninges with a fibroblast inducing agent comprising ascorbic acid.

16. The composition of claim 1, wherein said population of stem cells isolated from the meninges is obtained by a method, comprising:

obtaining meningeal tissue from a subject;

washing said meningeal tissue in a physiologic buffer to produce washed meningeal tissue; and placing said washed meningeal tissue on a culture substrate comprising a growth medium to culture said meningeal-derived stem cells.

17. The composition of claim 16, wherein said method further comprises:

placing said washed meningeal tissue in a solution comprising said physiologic buffer and collagenase to produce dissociated meningeal tissue; and recovering said dissociated meningeal tissue, and wherein placing said washed meningeal tissue on a culture substrate comprising a growth medium to culture said stem cells isolated from the meninges comprises plating said dissociated meningeal tissue onto a culture substrate comprising a growth medium.

18. The composition of claim 16, wherein obtaining said meningeal tissue is performed by biopsy from said subject, aseptic removal from said subject or both.

19. The composition of claim 16, wherein said physiologic buffer is selected from the group consisting of phosphate buffered saline (PBS), Hanks balanced salt solution and combinations thereof.

20. The composition of claim 17, wherein said culture substrate is selected from the group consisting of a tissue culture plate plastic, a laminin-covered substrate, a polyamino acid, a fibronectin, a type I collagen and combinations thereof.

21. The composition of claim 16, wherein said growth medium comprises Dulbecco's modified eagle medium (DMEM), about 10% fetal bovine serum (FBS) and about 1% glutamine.

\* \* \* \* \*